(12) United States Patent
McCarthy (10) Patent No.: US 10,912,405 B1
(45) Date of Patent: Feb. 9, 2021

(54) EXAMINATION GLOVE DONNING MACHINE

(71) Applicant: Eugene McCarthy, Rockville Centre, NY (US)

(72) Inventor: Eugene McCarthy, Rockville Centre, NY (US)

( * ) Notice: Subject to any disclaimer, the term of this patent is extended or adjusted under 35 U.S.C. 154(b) by 85 days.

(21) Appl. No.: 16/357,509

(22) Filed: Mar. 19, 2019

(51) Int. Cl.
*A47G 25/90* (2006.01)

(52) U.S. Cl.
CPC .................. *A47G 25/904* (2013.01)

(58) Field of Classification Search
CPC ........ A47G 25/90; A47G 25/904; B65H 1/08; B65H 3/46; B65H 20/02; B65D 83/00; B65D 83/0055; B65D 83/72; B65D 85/66; B65D 85/18; B65D 85/54; B65D 85/48; A61B 42/50; A61B 42/40; A61B 42/60; A61B 50/20; B25J 21/02; A41D 19/00; A41D 19/02; A41D 19/04; A41D 19/15; A41D 19/0068; A41D 19/0194; B26D 5/08; B26D 7/015; B26F 3/06
USPC ...................................... D29/117.1
See application file for complete search history.

(56) References Cited

U.S. PATENT DOCUMENTS

| 3,481,101 A | * | 12/1969 | Steadman | ............... B65B 11/52 |
| | | | | 53/471 |
| 3,625,790 A | * | 12/1971 | Ayres | ...................... B29C 66/43 |
| | | | | 156/93 |
| 3,748,939 A | * | 7/1973 | Feinstein | .................. B26D 5/08 |
| | | | | 83/370 |
| 4,773,532 A | | 9/1988 | Stephenson | |
| 4,889,266 A | | 12/1989 | Wright | |
| 4,915,272 A | | 4/1990 | Vlock | |
| 5,728,255 A | * | 3/1998 | Jurrius | .................... B29C 33/02 |
| | | | | 156/367 |
| 5,799,332 A | * | 9/1998 | Goodwin | ............. A41D 19/001 |
| | | | | 2/158 |
| 5,975,083 A | * | 11/1999 | Henderson, Jr. | ...... A41D 13/082 |
| | | | | 128/878 |
| 6,053,380 A | | 4/2000 | Sherrod | |
| 6,375,034 B1 | | 4/2002 | Corbett | |
| 6,868,999 B1 | * | 3/2005 | Gochanour | .......... A41D 13/082 |
| | | | | 128/879 |

(Continued)

FOREIGN PATENT DOCUMENTS

| JP | 6177490 B1 | * | 8/2017 |
| JP | 6411004 B1 | * | 10/2018 |
| WO | 0112032 | | 2/2001 |

*Primary Examiner* — Ismael Izaguirre (57) ABSTRACT

The examination glove donning machine is a mechanical device. The examination glove donning machine is configured for use with one or more hands of a patient. The examination glove donning machine comprises a housing, an elastomeric sheeting, a vacuum pump, and a laser cutting device. The housing contains the elastomeric sheeting, the vacuum pump, and the laser cutting device. The elastomeric sheeting forms a barrier around a hand of the patient. The vacuum pump creates a vacuum that draws the elastomeric sheeting around the hand of the patient. The laser cutting device cuts the elastomeric sheeting as it is drawn against the hand of the patient such that the examination glove is formed while on the hand of the patient. The examination glove donning machine simultaneously dons an examination glove on up to two hands of a patient.

16 Claims, 6 Drawing Sheets

(56) References Cited

U.S. PATENT DOCUMENTS

| | | | |
|---|---|---|---|
| 7,117,971 B1 * | 10/2006 | Cornacchia | A61B 7/02 |
| | | | 181/131 |
| 7,635,067 B1 | 12/2009 | Flynn | |
| 8,807,402 B2 | 8/2014 | Backhaus | |
| 9,957,125 B2 | 5/2018 | Ray | |
| 2002/0113079 A1 * | 8/2002 | Corbett | A47G 25/904 |
| | | | 221/303 |

* cited by examiner

EXAMINATION GLOVE DONNING MACHINE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of domestic articles including items configured for use in donning apparel, more specifically, a device for donning a glove. (A47G25/904)

SUMMARY OF INVENTION

The examination glove donning machine is a mechanical device. The examination glove donning machine is configured for use with a patient. The examination glove donning machine dons an examination glove on one or more hands of the patient. The examination glove donning machine comprises a housing, an elastomeric sheeting, a vacuum pump, and a laser cutting device. The housing contains the elastomeric sheeting, the vacuum pump, and the laser cutting device. The elastomeric sheeting forms a barrier around a hand of the patient. The vacuum pump creates a vacuum that draws the elastomeric sheeting around the hand of the patient. The laser cutting device cuts the elastomeric sheeting as it is drawn against the hand of the patient such that the examination glove is formed while on the hand of the patient. The examination glove donning machine simultaneously dons an examination glove on up to two hands of a patient.

These together with additional objects, features and advantages of the examination glove donning machine will be readily apparent to those of ordinary skill in the art upon reading the following detailed description of the presently preferred, but nonetheless illustrative, embodiments when taken in conjunction with the accompanying drawings.

In this respect, before explaining the current embodiments of the examination glove donning machine in detail, it is to be understood that the examination glove donning machine is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the examination glove donning machine.

It is therefore important that the claims be regarded as including such equivalent construction insofar as they do not depart from the spirit and scope of the examination glove donning machine. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
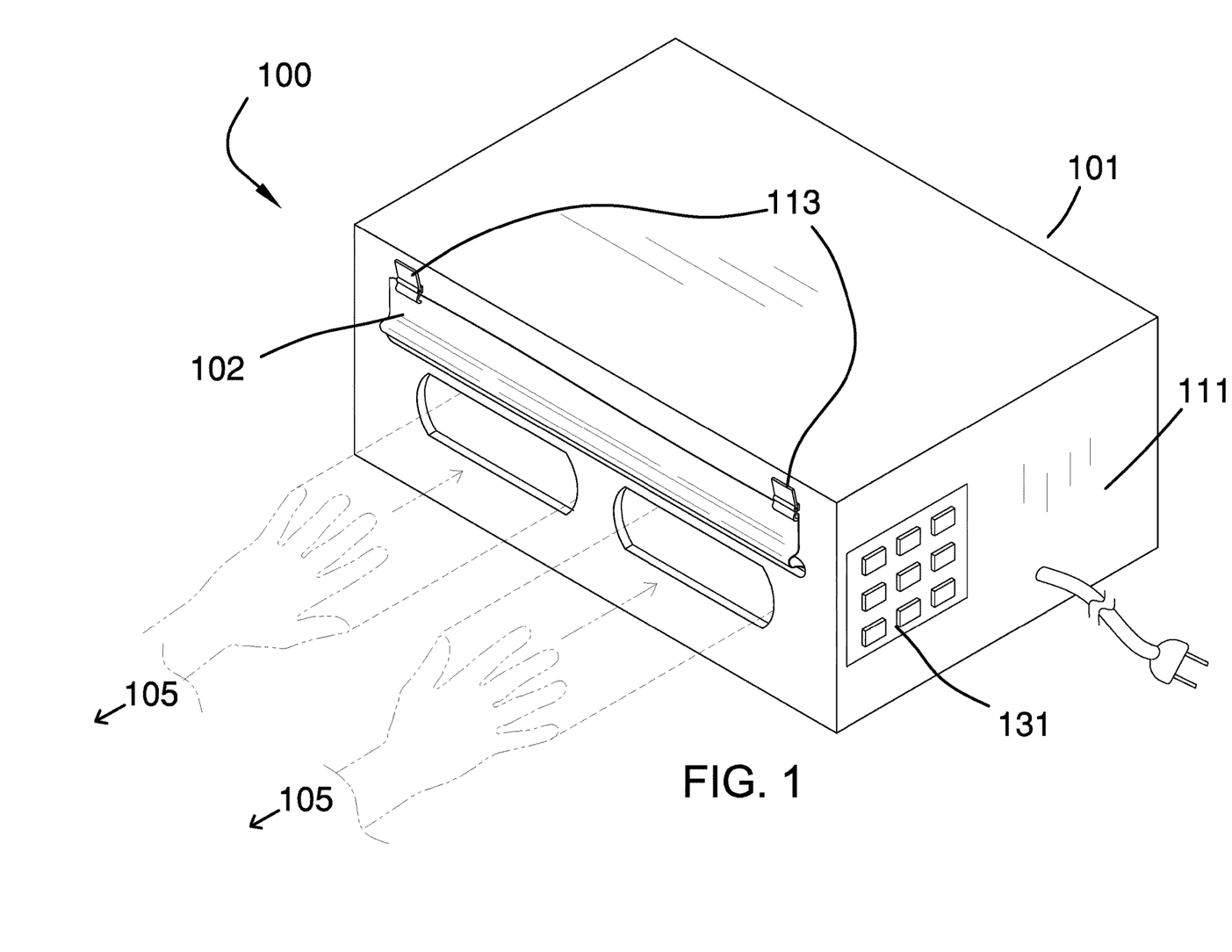
FIG. 1 is a perspective view of an embodiment of the disclosure.
Figure 2:
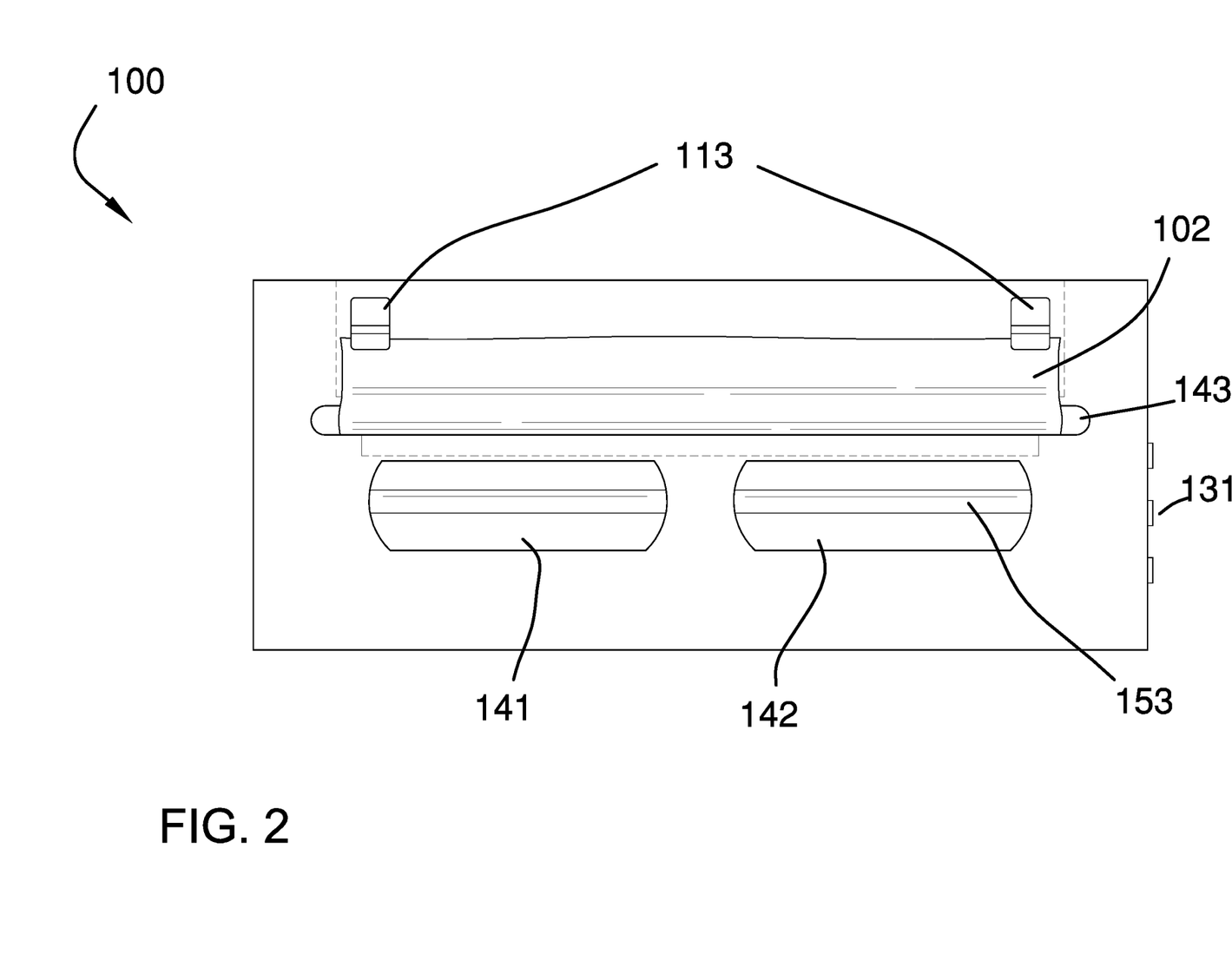
FIG. 2 is a front view of an embodiment of the disclosure.
Figure 3:
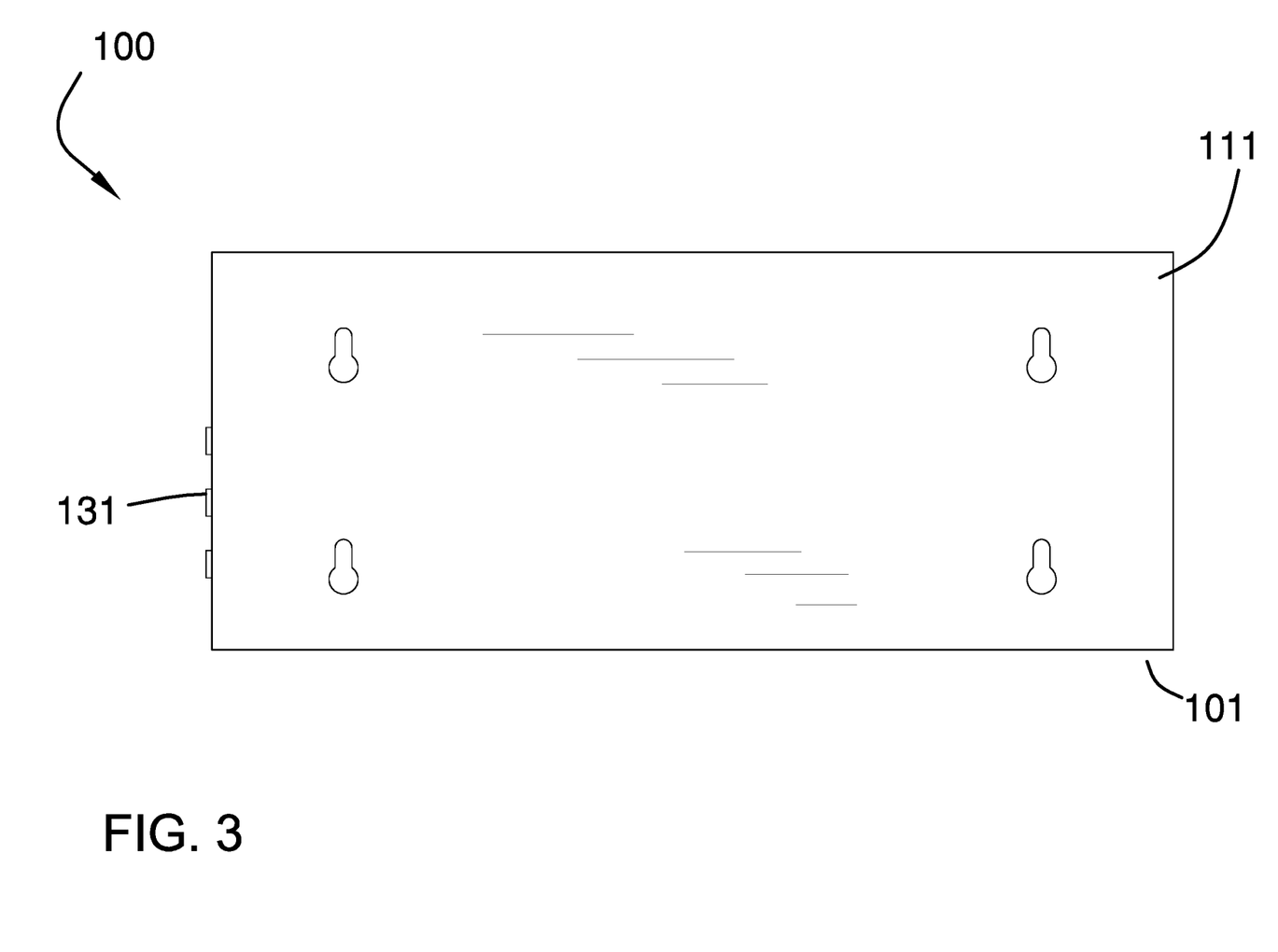
FIG. 3 is a rear view of an embodiment of the disclosure.
Figure 4:
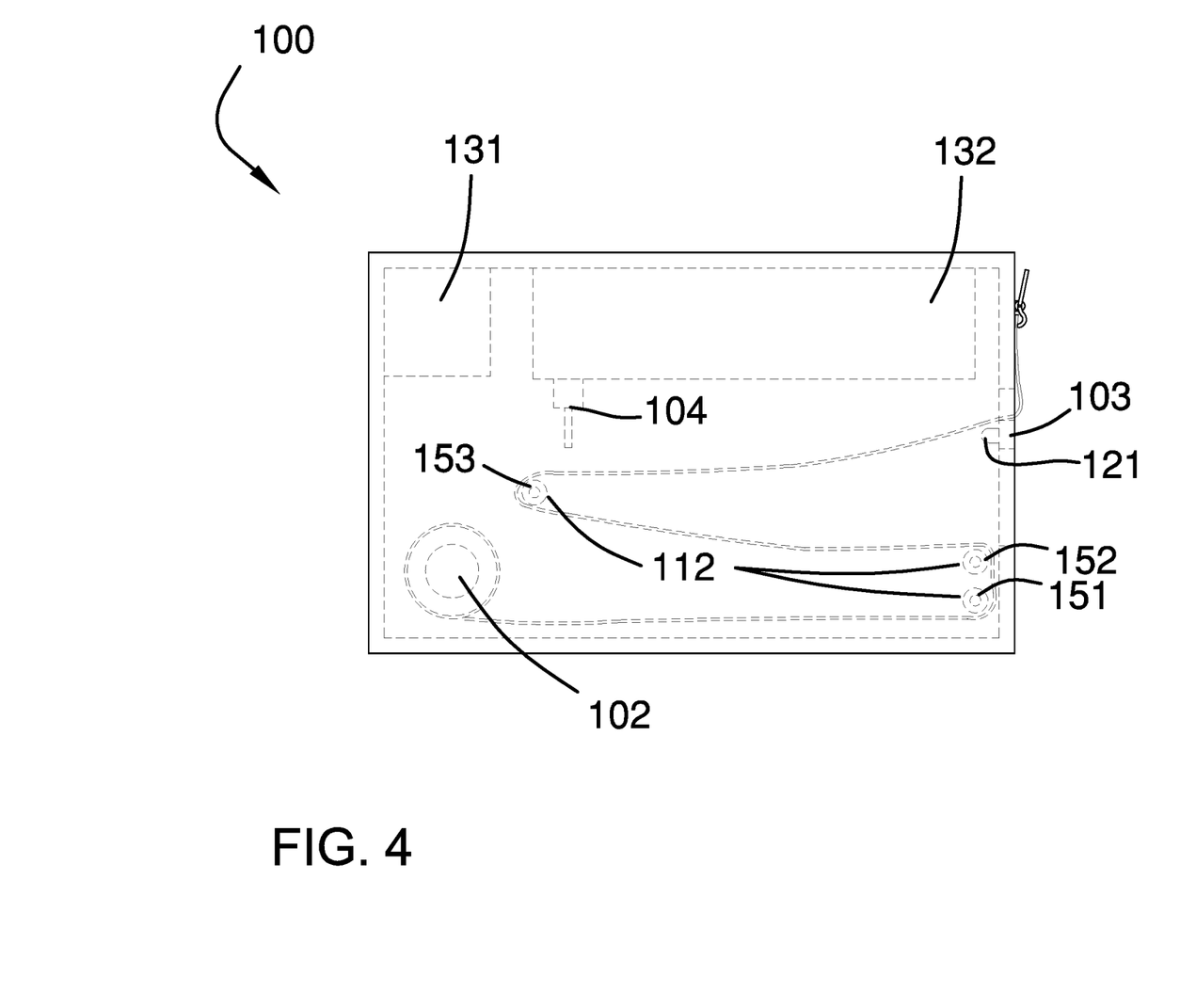
FIG. 4 is a side view of an embodiment of the disclosure.
Figure 5:
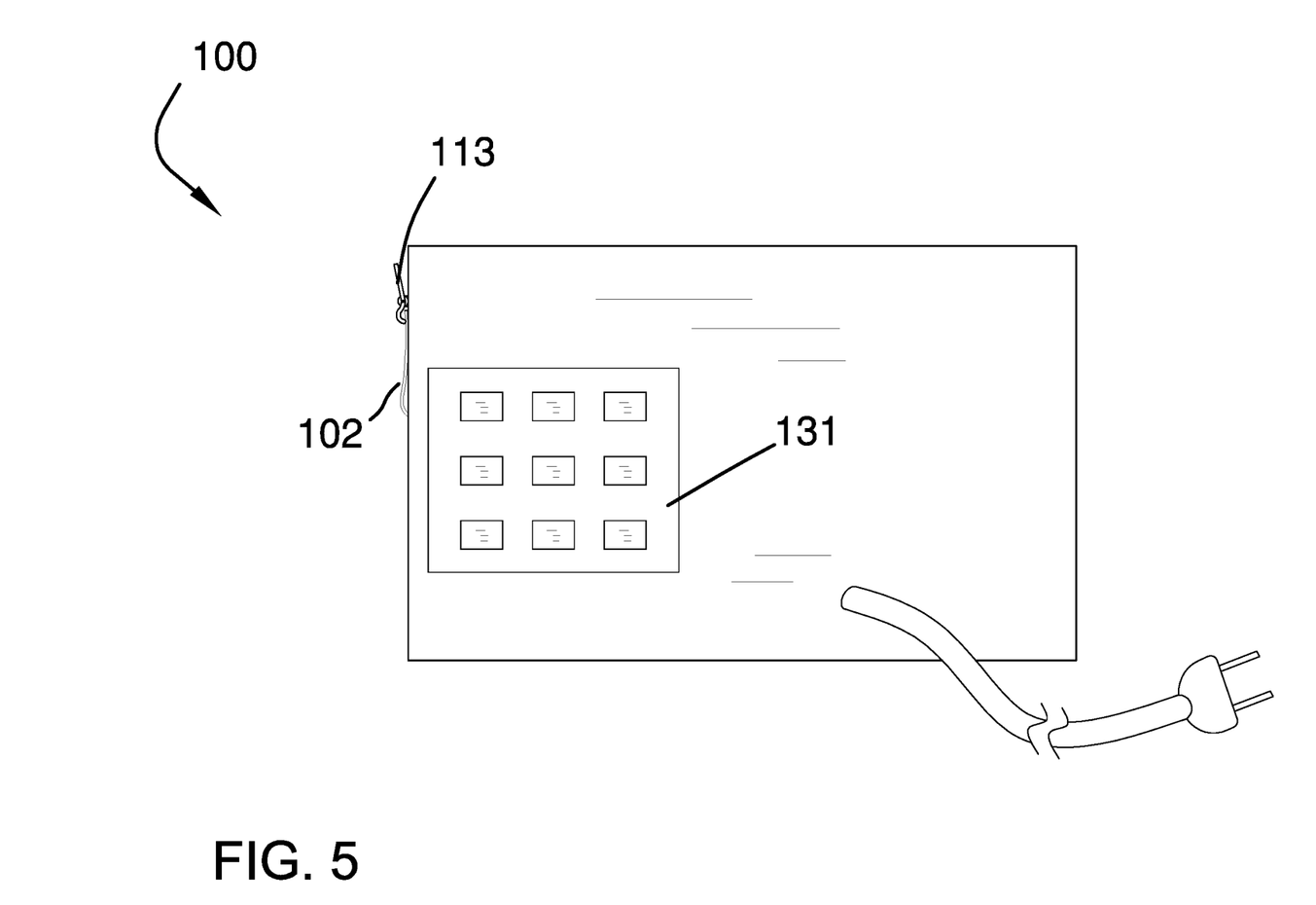
FIG. 5 is a reverse side view of an embodiment of the disclosure.
Figure 6:
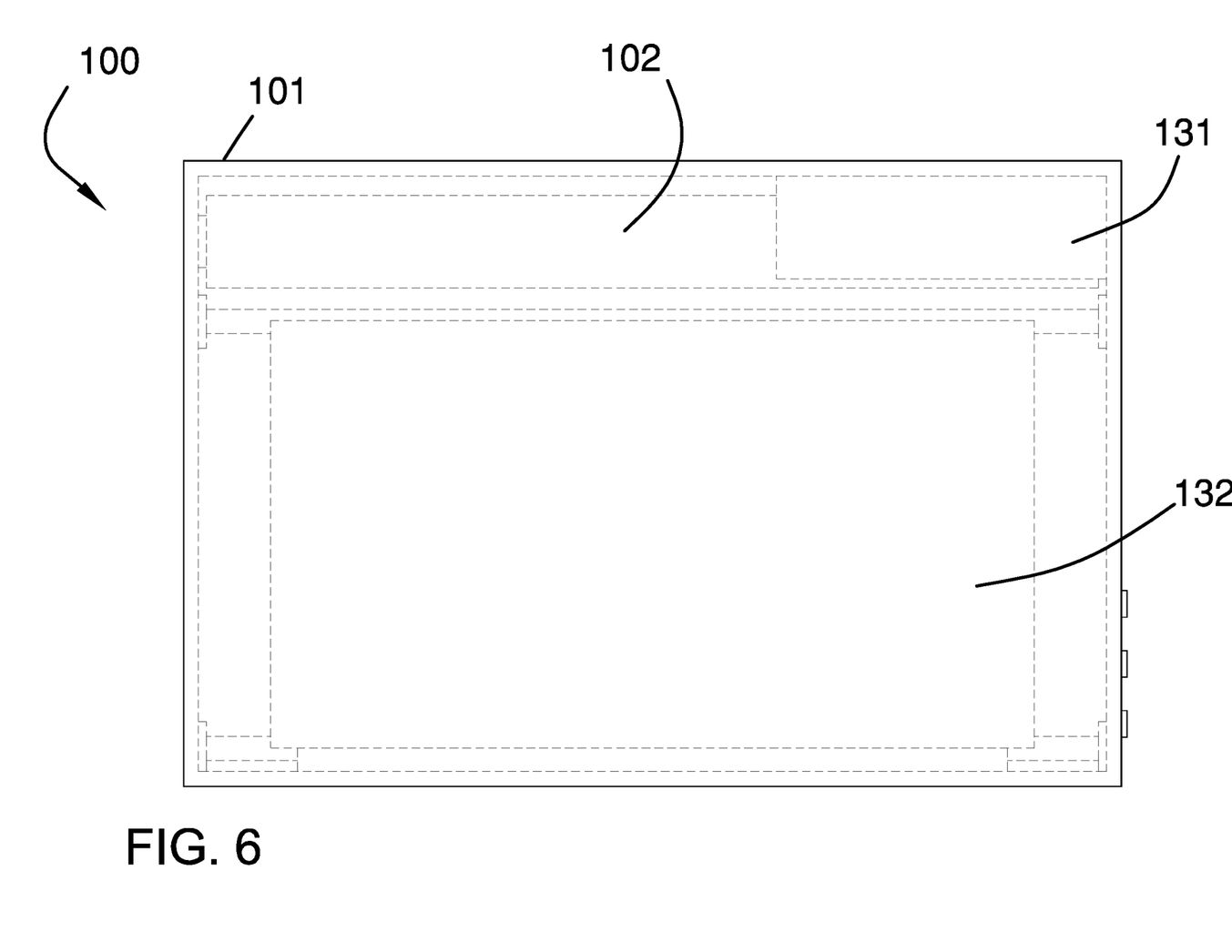
FIG. 6 is a top view of an embodiment of the disclosure.

Detailed reference will now be made to one or more potential embodiments of the disclosure, which are illustrated in FIGS. 1 through 6.

The examination glove donning machine 100 (hereinafter invention) is a mechanical device. The invention 100 is configured for use with a patient 105. The invention 100 dons an examination glove on one or more hands 106 of the patient 105. The invention 100 comprises a housing 101, an elastomeric sheeting 102, a vacuum pump 103, and a laser cutting device 104. The housing 101 contains the elastomeric sheeting 102, the vacuum pump 103, and the laser cutting device 104. The elastomeric sheeting 102 forms a barrier around a hand of the patient 105. The vacuum pump 103 creates a vacuum that draws the elastomeric sheeting 102 around the hand of the patient 105. The laser cutting device 104 cuts the elastomeric sheeting 102 as it is drawn against the hand of the patient 105 such that the examination glove is formed while on the hand of the patient 105. The invention 100 simultaneously dons an examination glove on up to two hands of a patient 105.

The housing 101 is a hollow containment structure. The housing 101 is a casing. The housing 101 contains the elastomeric sheeting 102, the vacuum pump 103, and the laser cutting device 104. The housing 101 is formed with all apertures and form factors necessary to allow the housing 101 to accommodate the use and operation of the invention 100. The patient 105 places one or more hands 106 into the housing 101 such that the elastomeric sheeting 102, the vacuum pump 103, and the laser cutting device 104 don an examination glove on the one or more hands 106 of the patient 105. Methods to form a housing 101 suitable for the purposes described in this disclosure are well-known and documented in the mechanical arts. The housing comprises an exterior shell 111, a plurality of rollers 112, and a sheeting clip 113.

The exterior shell 111 forms the physical containment structure of the housing 101. The exterior shell 111 is a casing. The exterior shell 111 contains the elastomeric sheeting 102, the vacuum pump 103, and the laser cutting device 104. The exterior shell 111 is formed with all apertures and form factors necessary to allow the exterior shell 111 to accommodate the use and operation of the elastomeric sheeting 102, the vacuum pump 103, and the laser cutting device 104. Methods to form an exterior shell 111 suitable for the purposes described in this disclosure are well-known and documented in the mechanical arts. The exterior shell 111 further comprises a first patient aperture 141, a second patient aperture 142, and a sheeting aperture 143.

The first patient aperture 141 is an aperture that is formed through the exterior shell 111. The first patient aperture 141 is sized to receive a hand of the one or more hands 106 of the patient 105. The first patient aperture 141 is positioned such that the selected hand inserts between two sheets of the elastomeric sheeting 102 that is threaded through the track formed by the plurality of rollers 112.

The second patient aperture 142 is an aperture that is formed through the exterior shell 111. The second patient aperture 142 is sized to receive a hand of the one or more hands 106 of the patient 105. The second patient aperture 142 is positioned such that the selected hand inserts between two sheets of the elastomeric sheeting 102 that is threaded through the track formed by the plurality of rollers 112.

The sheeting aperture 143 is an aperture that is formed through the exterior shell 111. The sheeting aperture 143 is positioned proximal to the sheeting clip 113. The elastomeric sheeting 102 inserts through the sheeting aperture 143 before attaching to the sheeting clip 113.

Each of the plurality of rollers 112 is a rotating shaft. Each of the plurality of rollers 112 are mounted in the interior space formed by the exterior shell 111. The plurality of rollers 112 combine to form a track through which the elastomeric sheeting 102 is threaded. The plurality of rollers 112 are positioned such that the one or more hands 106 of the patient 105 insert between two layers of the elastomeric sheeting 102 before the formation of the examination glove by the invention 100. The plurality of rollers 112 further comprises an inferior roller 151, a superior roller 152, and an interior roller 153.

The inferior roller 151 is the roller selected from the plurality of rollers 112 with the lowest elevation. The inferior roller 151 mounts on the interior surface of the face that contains the exterior shell 111 that contains the first patient aperture 141, the second patient aperture 142, and the sheeting aperture 143. The inferior roller 151 receives the elastomeric sheeting 102 directly from the roll and changes the direction of travel of the elastomeric sheeting 102 toward the superior roller 152.

The superior roller 152 is the roller selected from the plurality of rollers 112 with an elevation between the elevations of the inferior roller 151 and the interior roller 153. The superior roller 152 mounts on the interior surface of the face that contains the exterior shell 111 that contains the first patient aperture 141, the second patient aperture 142, and the sheeting aperture 143. The superior roller 152 receives the elastomeric sheeting 102 directly from the inferior roller 151 and changes the direction of travel of the elastomeric sheeting 102 towards the superior roller 152.

The interior roller 153 is the roller selected from the plurality of rollers 112 with the highest elevation. The interior roller 153 mounts across the hollow interior of the exterior shell 111. The interior roller 153 receives the elastomeric sheeting 102 directly from the superior roller 152 and changes the direction of travel of the elastomeric sheeting 102 towards the sheeting clip 113 and the sheeting aperture 143. The interior roller 153 forms the sheeting overlay of the elastomeric sheeting 102 used to enclose the one or more hands 106 with a barrier formed by the elastomeric sheeting 102.

The sheeting clip 113 is a spring-loaded device that attaches to the exterior shell 111 of the housing 101. The position of the sheeting clip 113 is proximal to the location of the sheeting aperture 143. The sheeting clip 113 acts as a spring. Specifically, when the elastomeric sheeting 102 inserts between the sheeting clip 113 and the exterior shell 111, the sheeting clip 113 applies a force that secures the elastomeric sheeting 102 to the exterior shell 111.

The elastomeric sheeting 102 is a commercially available sheeting that is formed from an elastomeric material. The elastomeric sheeting 102 is formed from a fluid impermeable plastic. The elastomeric sheeting 102 is stored on a roll. The elastomeric sheeting 102 is wrapped around the one or more hands 106 of the patient 105 to form an examination glove. The elastomeric sheeting 102 is fitted individually to a hand selected from the one or more hands 106 of the patient 105 by the vacuum pump 103 and the laser cutting device 104.

The vacuum pump 103 is a mechanical device. The vacuum pump 103 creates a pressure differential across the face of the elastomeric sheeting 102 such that the vacuum pump 103 draws air away from the elastomeric sheeting 102 such that the elastomeric sheeting 102 is sealed to the one or more hands 106 of the patient 105. The vacuum pump 103 further comprises a vacuum tube 121.

The vacuum tube 121 is a hose. The vacuum tube 121 forms a fluidic connection from a position between the overlaid sheets of the elastomeric sheeting 102 and the vacuum pump 103 such that the vacuum pump 103 will draw the contained space formed by the elastomeric sheeting 102 around the one or more hands 106 of the patient 105.

The laser cutting device 104 is a laser device used to cut the elastomeric sheeting 102 into a form that allows the elastomeric sheeting 102 to form a seal that allows a vacuum to be formed within the elastomeric sheeting 102. The laser cutting device 104 cuts a seam into the elastomeric sheeting 102 after the elastomeric sheeting 102 is overlaid upon itself. The laser cutting device 104 cuts an initial seam that encloses the elastomeric sheeting 102 such that a vacuum can be drawn with an enclosed space formed within the initially cut section of the elastomeric sheeting 102. The laser cutting device 104 cuts a subsequent seam that encloses the elastomeric sheeting 102 around the one or more hands 106 after the vacuum pump 103 form fits the elastomeric sheeting 102 to the one or more hands 106 of the patient 105. The subsequent seam cut by the laser cutting device 104 is the final step in the formation of the examination glove.

The laser cutting device 104 further comprises a tracking system 131 and an XY gantry 132.

The tracking system 131 is an electrical circuit. The tracking system 131 controls the position of the laser cutting device 104 in the XY gantry 132. The tracking system 131 controls the operation of the laser cutting device 104 such that the tracking system 131 will cut all the seams necessary to form the examination glove around the one or more hands 106 of the patient 105 without injuring the patient 105. Methods to form the tracking system 131 described in this paragraph are well-known and documented in the electrical arts.

In the first potential embodiment of the disclosure, the laser cutting device 104 is suspended the superior interior surface of the housing 101 by the XY gantry 132. The XY gantry 132 is defined in greater detail elsewhere in this disclosure. The XY gantry 132 moves the laser cutting device 104 within the interior space of the housing 101 such that the location of each of the cuts and seams formed by the laser cutting device 104 can be controlled by the XY gantry 132.

The following definitions were used in this disclosure:

Clip: As used in this disclosure, a clip is a fastener that attaches to an object by gripping or clasping the object. A clip is typically spring loaded.

Copolymer: As used in this disclosure, a copolymer is a polymer formed from two or more repeating molecules (also referred to as monomers).

Don: As used in this disclosure, to don means to put a garment on a person.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Fluid: As used in this disclosure, a fluid refers to a state of matter wherein the matter is capable of flow and takes the shape of a container it is placed within. The term fluid commonly refers to a liquid or a gas.

Fluidic Connection: As used in this disclosure, a fluidic connection refers to a tubular structure that transports a fluid from a first object to a second object. Methods to design and use a fluidic connections are well-known and documented in the mechanical, chemical, and plumbing arts.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Gantry: As used in this disclosure, a gantry is an elevated structure from which a handling system is suspended. Specifically: 1) the gantry forms the superior end of a hypothetical prism formed between the gantry and an inferior end projected onto the supporting surface underneath the gantry; wherein, 2a) the material handling system can capture material to be handled that is contained at a point within the hypothetical prism boundaries; wherein 2b) the material handling system can release previously captured material at a point within the hypothetical prism boundaries; and wherein, 2c) the material handling system can transport the previously captured material from the capture point to the release point; and, 3) the load path that supports the gantry is external to the hypothetical prism boundaries. An XY gantry is a gantry that can: 1) capture material from any location within the hypothetical prism; 2) release previously captured material at any location within the hypothetical prism; and, 3) can transport the previously captured material from any capture point location within the hypothetical prism to any release point location within the hypothetical prism. The use of a gantry is well-known in the mechanical arts and the material handling fields.

Gas: As used in this disclosure, a gas refers to a state (phase) of matter that is fluid and that fills the volume of the structure that contains it. Stated differently, the volume of a gas always equals the volume of its container.

Glove: As used in this disclosure, a glove is an item of apparel that covers a hand. The glove comprises five finger stalls into which the fingers of the hand are inserted. A glove is further defined with a palm side and a back side. The palm side is proximal to the palm of the hand. The back side is distal from the palm side.

Hose: As used in this disclosure, a hose is a flexible hollow prism-shaped device that is used for transporting liquids and gases. When referring to a hose in this disclosure, the terms inner dimension and outer dimension are used as they would be used by those skilled in the plumbing arts.

Housing: As used in this disclosure, a housing is a rigid casing that encloses and protects one or more devices.

Inferior: As used in this disclosure, the term inferior refers to a directional reference that is parallel to and in the same direction as the force of gravity when an object is positioned or used normally.

Liquid: As used in this disclosure, a liquid refers to a state (phase) of matter that is fluid and that maintains, for a given pressure, a fixed volume that is independent of the volume of the container.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Monomer: As used in this disclosure, a monomer refers to a molecular structure that bonds to itself in a repeating manner to form a polymer.

Organic: As used in this disclosure, organic refers to a carbon-based chemical structure. A limited number of carbon-based salts are traditionally considered inorganic chemical structures and are excluded from the study of organic chemistry.

Patient: As used in this disclosure, a patient is a person who is designated to receive a medical treatment, therapy or service. The term patient may be extended to an animal when used within the context of the animal receiving veterinary treatment or services.

Plastic: As used in this disclosure, plastic refers to a manufactured material that is formed from a structure selected from the group consisting of a polymer or a copolymer. Unless stated otherwise, this disclosure assumes that the plastic is formed from organic monomers.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Polymer: As used in this disclosure, a polymer refers to a molecular chain that comprises multiple repeating units known as monomers. The repeating unit may be an atom or a molecular structure.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Relaxed Shape: As used in this disclosure, a structure is considered to be in its relaxed state when no shear, strain, or torsional forces are being applied to the structure.

Roll: As used in this disclosure, a roll is a method of storing paper or other sheeting in a cylindrical structure such that creases are not formed within the paper or sheeting. To form the roll, the paper or other sheeting material is curved over itself around a center axis such that a spiral is formed when the roll is viewed from the end of the cylindrical structure.

Roller: As used in this disclosure, a roller is rotating cylindrical or disk structure used to reduce the friction of movement of an object supported by the roller. A roller will often change the direction of a cord or sheeting.

Sheeting: As used in this disclosure, a sheeting is a material, such as a paper, textile, a plastic, or a metal foil, in the form of a thin flexible layer or layers.

Shell: As used in this disclosure, a shell refers to the exterior surfaces of an object.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Superior: As used in this disclosure, the term superior refers to a directional reference that is parallel to and in the opposite direction of the force of gravity when an object is positioned or used normally.

Suspend: As used in this disclosure, to suspend an object means to support an object such that the inferior end of the object does not form a significant portion of the load path of the object. Include inferior superior and load path.

Thread: As used in this disclosure, to thread is a verb that refers to inserting a sheeting through a track.

Track: As used in this disclosure, a track is a device that is used to control the path of motion of an object.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A glove donning machine comprising
a housing, an elastomeric sheeting, a vacuum pump, and a laser cutting device;
wherein the housing contains the elastomeric sheeting, the vacuum pump, and the laser cutting device;
wherein the glove donning machine is a mechanical device;
wherein the glove donning machine is configured for use with a patient;
wherein the glove donning machine dons an examination glove on one or more hands of the patient;
wherein the elastomeric sheeting forms a barrier around a hand of the patient;
wherein the vacuum pump creates a vacuum that draws the elastomeric sheeting around the hand of the patient;
wherein the laser cutting device cuts the elastomeric sheeting as it is drawn against the hand of the patient such that the examination glove is formed while on the hand of the patient;
wherein the glove donning machine simultaneously dons an examination glove on up to two hands of a patient;
wherein the housing is a hollow containment structure;
wherein the patient places one or more hands into the housing such that the elastomeric sheeting, the vacuum pump, and the laser cutting device don the examination glove on the one or more hands of the patient;
wherein the housing comprises an exterior shell, a plurality of rollers, and a sheeting clip;
wherein the plurality of rollers install in the exterior shell;
wherein the sheeting clip attaches to the exterior shell.

2. The glove donning machine according to claim 1
wherein the exterior shell forms the physical containment structure of the housing;
wherein the exterior shell contains the elastomeric sheeting, the vacuum pump, and the laser cutting device.

3. The glove donning machine according to claim 2
wherein the exterior shell further comprises a first patient aperture, a second patient aperture, and a sheeting aperture;
wherein the first patient aperture is an aperture that is formed through the exterior shell;
wherein the second patient aperture is an aperture that is formed through the exterior shell;
wherein the sheeting aperture is an aperture that is formed through the exterior shell;
wherein the sheeting aperture is positioned proximal to the sheeting clip.

4. The glove donning machine according to claim 3
wherein the first patient aperture is sized to receive a hand of the one or more hands of the patient;

wherein the first patient aperture is positioned such that the selected hand inserts between two sheets of the elastomeric sheeting that is threaded through the track formed by the plurality of rollers;

wherein the second patient aperture is sized to receive a hand of the one or more hands of the patient;

wherein the second patient aperture is positioned such that the selected hand inserts between two sheets of the elastomeric sheeting that is threaded through the track formed by the plurality of rollers.

5. The glove donning machine according to claim 4 wherein the elastomeric sheeting inserts through the sheeting aperture before attaching to the sheeting clip.

6. The glove donning machine according to claim 5 wherein each of the plurality of rollers is a rotating shaft;

wherein each of the plurality of rollers are mounted in the interior space formed by the exterior shell;

wherein the plurality of rollers combine to form a track through which the elastomeric sheeting is threaded.

7. The glove donning machine according to claim 6 wherein the plurality of rollers are positioned such that the one or more hands of the patient insert between two layers of the elastomeric sheeting before the formation of the examination glove by the glove donning machine.

8. The glove donning machine according to claim 7 wherein the plurality of rollers further comprises an inferior roller, a superior roller, and an interior roller;

wherein the inferior roller is the roller selected from the plurality of rollers with the lowest elevation;

wherein the inferior roller mounts on the interior surface of the face that contains the exterior shell that contains the first patient aperture, the second patient aperture, and the sheeting aperture;

wherein the superior roller is the roller selected from the plurality of rollers with an elevation between the elevations of the inferior roller and the interior roller;

wherein the interior roller is the roller selected from the plurality of rollers with the highest elevation.

9. The glove donning machine according to claim 8 wherein the inferior roller receives the elastomeric sheeting directly from the roll and changes the direction of travel of the elastomeric sheeting toward the superior roller;

wherein the superior roller mounts on the interior surface of the face that contains the exterior shell that contains the first patient aperture, the second patient aperture, and the sheeting aperture;

wherein the superior roller receives the elastomeric sheeting directly from the inferior roller and changes the direction of travel of the elastomeric sheeting towards the superior roller;

wherein the interior roller mounts across the hollow interior of the exterior shell;

wherein the interior roller receives the elastomeric sheeting directly from the superior roller and changes the direction of travel of the elastomeric sheeting towards the sheeting clip and the sheeting aperture;

wherein the interior roller forms the sheeting overlay of the elastomeric sheeting used to enclose the one or more hands with a barrier formed by the elastomeric sheeting.

10. The glove donning machine according to claim 9 wherein the sheeting clip is a spring-loaded device that attaches to the exterior shell of the housing;

wherein the position of the sheeting clip is proximal to the location of the sheeting aperture;

wherein the sheeting clip is a spring;

wherein the elastomeric sheeting inserts between the sheeting clip and the exterior shell.

11. The glove donning machine according to claim 10 wherein the elastomeric sheeting is a sheeting that is formed from an elastomeric material;

wherein the elastomeric sheeting is formed from a fluid impermeable plastic;

wherein the elastomeric sheeting is stored on a roll;

wherein the elastomeric sheeting is wrapped around the one or more hands of the patient to form the examination glove;

wherein the elastomeric sheeting is fitted individually to a hand selected from the one or more hands of the patient by the vacuum pump and the laser cutting device;

wherein the elastomeric sheeting is a sheeting that is formed from an elastomeric material;

wherein the elastomeric sheeting is formed from a fluid impermeable plastic;

wherein the elastomeric sheeting is stored on a roll.

12. The glove donning machine according to claim 11 wherein the vacuum pump is a mechanical device;

wherein the vacuum pump creates a pressure differential across the face of the elastomeric sheeting such that the vacuum pump draws air away from the elastomeric sheeting such that the elastomeric sheeting is sealed to the one or more hands of the patient.

13. The glove donning machine according to claim 12 wherein the vacuum pump further comprises a vacuum tube;

wherein the vacuum tube is a hose;

wherein the vacuum tube forms a fluidic connection from a position between the overlaid sheets of the elastomeric sheeting and the vacuum pump such that the vacuum pump will draw the contained space formed by the elastomeric sheeting around the one or more hands of the patient.

14. The glove donning machine according to claim 13 wherein the laser cutting device is a laser device used to cut the elastomeric sheeting into a form a seam;

wherein the laser cutting device cuts a seam into the elastomeric sheeting after the elastomeric sheeting is overlaid upon itself.

15. The glove donning machine according to claim 14 wherein the laser cutting device cuts an initial seam that encloses the elastomeric sheeting such that a vacuum can be drawn with an enclosed space formed within the initially cut section of the elastomeric sheeting;

wherein the laser cutting device cuts a subsequent seam that encloses the elastomeric sheeting around the one or more hands after the vacuum pump form fits the elastomeric sheeting to the one or more hands of the patient.

16. The glove donning machine according to claim 15 wherein the laser cutting device further comprises a tracking system and an XY gantry;

wherein the tracking system is an electrical circuit;

wherein the tracking system controls the position of the laser cutting device in the XY gantry;

wherein the tracking system controls the operation of the laser cutting device such that the tracking system will cut all the seams necessary to form the examination glove around the one or more hands of the patient without injuring the patient;

wherein the laser cutting device is suspended the superior interior surface of the housing by the XY gantry;

wherein the XY gantry moves the laser cutting device within the interior space of the housing such that the location of each of the cuts and seams formed by the laser cutting device can be controlled by the XY gantry.

* * * * *